US006390659B1

(12) United States Patent
Saad et al.

(10) Patent No.: US 6,390,659 B1
(45) Date of Patent: May 21, 2002

(54) LIGHT HANDLE HAVING BENDABLE SHIELD

(75) Inventors: Steve Edward Saad, Powell; William G. Pittman, Knoxville, both of TN (US)

(73) Assignee: DeRoyal Industries, Inc., Powell, TN (US)

(*) Notice: Subject to any disclaimer, the term of this patent is extended or adjusted under 35 U.S.C. 154(b) by 0 days.

(21) Appl. No.: 09/557,167

(22) Filed: Apr. 25, 2000

(51) Int. Cl.[7] .................................................. A61B 1/06
(52) U.S. Cl. ........................ 362/572; 362/399; 362/400; 362/804; 206/438
(58) Field of Search ................................. 362/399, 400, 362/804; 206/438, 223

(56) References Cited

U.S. PATENT DOCUMENTS

| | | | | |
|---|---|---|---|---|
| 4,605,124 A | | 8/1986 | Sandel et al. | |
| 4,844,252 A | * | 7/1989 | Barron et al. | 206/223 |
| 4,878,156 A | | 10/1989 | Hallings et al. | |
| 4,974,288 A | | 12/1990 | Reasner | |
| 4,976,299 A | | 12/1990 | Bickelman | |
| D313,670 S | | 1/1991 | Barron et al. | |
| 5,036,446 A | | 7/1991 | Quintanilla et al. | |
| 5,065,296 A | | 11/1991 | Cude | |
| 5,273,157 A | | 12/1993 | Spina | |
| 5,355,292 A | | 10/1994 | Hoftman et al. | |
| 5,469,600 A | | 11/1995 | Sandel | |
| 5,493,757 A | | 2/1996 | Horan et al. | |
| 5,604,955 A | | 2/1997 | Horan | |
| 5,669,102 A | | 9/1997 | Sandel | |
| 5,697,123 A | | 12/1997 | Gharibian et al. | |
| 5,700,085 A | * | 12/1997 | Calderwood | 362/399 |
| 5,709,465 A | | 1/1998 | Lanzone | |
| 5,735,598 A | | 4/1998 | Ramirez | |

* cited by examiner

*Primary Examiner*—Sandra O'Shea
*Assistant Examiner*—Bertrand Zeade
(74) *Attorney, Agent, or Firm*—Pitts & Brittian, P.C.

(57) ABSTRACT

A disposable light handle is designed for removable attachment to manually adjustable light fixtures employed in sterile medical settings. The light handle includes an elongated handle body, having one end closed, and an opposite end provided with a threaded portion. At the junction of handle body and threaded portion is an integrally formed circular shield that projects therefrom to provide a guard against contact between the hand of a user and the light fixture. The shield is sufficiently resilient and flexible to permit opposite sides of an outer periphery to bend into an overlying relationship to the handle body for minimizing width in storage. The shield is provided with loops located diametrically opposed to one another on the periphery of the shield. Connector projections are diametrically opposed to one another along the length of the handle body, and positioned to releasably receive thereon the loops when the shield is bent into an overlying relationship. Light handles are interconnectable in a package by providing an elongated groove originating in the closed end of each handle body and extending along a portion of the length of the surface of each handle body, and an insert projection on a surface substantially opposite the elongated groove of each handle body. The insert projection of one handle body is inerrable into the elongated groove of a second handle body, thereby allowing interconnection for minimizing space in packaging.

35 Claims, 12 Drawing Sheets

LIGHT HANDLE HAVING BENDABLE SHIELD

FIELD OF INVENTION

The present invention relates to disposable light handles for manually adjustable light fixtures utilized in sterile medical treatment and operating rooms, for example.

BACKGROUND OF INVENTION

In the field of disposable light handles, sterile light handles may be designed to provide ease of connection with light fixtures to allow medical personnel to maintain sterile conditions and to control movable light fixtures in medical operating rooms. It is a preference in the field that the disposable light handles can be compactly containerized for space-efficient storage and shipment while maintaining sterility of the light handles.

Typical of the prior art are those disposable light handles disclosed in the following U.S. Patents. In U.S. Pat. No. 5,735,598, to Ramirez, a surgical light handle is disclosed that includes a tubular handle, a circular generally planar shield, and a threaded portion. The circular shield includes two living hinges which permit opposing sides of the shield to be folded down against the handle for packaging and storage. These folded sides will not return to the plane of the shield of their own accord and require some external force for their alignment as parts of the shield. A plurality of tabs are disposed on the lower face of the shield, and a matching indentation is formed on the lower end of the handle to enable two side-by-side aligned handles to be frictionally engaged together as a unit by engaging the tabs of one handle with the indentations of the other handle. The circular shield is spread and held in an open configuration when the handle is attached to a separate adapter cap that provides tension against a central portion of the shield to return the folded sides of the shield to the plane of the circular shield, and attaches the handle and shield to a light fixture handle.

In U.S. Pat. No. 4,974,288, to Reasner, a disposable plastic handle and shield for engaging a surgical light fixture handle is disclosed that includes a hollow handle with a threaded upper end portion and an integral, generally planar circular shield connected to the handle between the threaded upper end portion and the lower portion of the hollow handle. The shield includes a pair of spaced apart grooves in the shield underside to allow opposite sides of the shield to be folded downward onto the lower portion of the hollow handle for packaging and storage. Return of the downwardly folded sides of the shield to the plane of the circular shield is by mechanical leverage applied through an adaptor.

In U.S. Pat. No. 4,878,156, to Hallings et al., a quick release focusing handle for surgical lights is disclosed that includes a hollow handle with an attachable end that encircles the focusing handle of the light. The attachable end includes a tensioning screw that is tightened against the focusing handle, and a circular shield that is attachable distal of the tensioning screw along the hollow handle. The shield is detachable as a unit from the hollow handle for packaging and storage.

In U.S. Pat. No. 4,844,252, to Barron et al., a sterilizable multi-part handle for attachment to surgery room light fixtures is disclosed that includes a handle body portion, an end having a threaded head portion, and a separate circular disc that fits onto the threaded head portion end. The handle body portion is packaged by stacking of discs and handle bodies side-by-side with a retainer strap encircling the handle bodies.

Accordingly, there is a need for an improved disposable light handle that connects with a light fixture, that can be compactly containerized for space-efficient and sterile storage and shipment until utilized in sterile medical environments, and that provides ease of unpackaging and assembly by sterile gloved medical personnel.

Therefore, it is an object of the present invention to provide a disposable light handle.

It is another object of the present invention to provide a light handle that may be packaged in a sterile, space efficient configuration to minimize the volume of stored handle.

It is another object of the present invention to provide a disposable light handle that provides ease of gripping in moist environments, and fits onto a multitude of light fixtures.

It is another object of the present invention to provide a disposable light handle that is easily removed from packaging and assembled by gloved medical personnel in sterile environments.

SUMMARY OF INVENTION

In accordance with the present invention, there is provided a disposable light handle for attachment to a manually adjustable light fixture such as light fixtures employed in surgical suites, dental offices and sterile medical settings. The present handle is designed to be removably attached to the light fixture employing an existing threaded attachment means on the light fixture and a mating threaded end of the disposable handle, and/or an adaptor interposed between the disposable handle and the light fixture attachment means.

The disposable light handle of the present invention includes an elongated handle portion, one end of which is closed, and the opposite open end of which is provided with a threaded portion. At the junction of the handle portion and the threaded portion there is provided a generally circular shield that is integrally formed with the handle portion and projects radially therefrom to provide a guard against contact between the hand of a user and the light fixture during attachment of the handle to the light fixture, and during grasping of the handle by the user for adjustment of the light fixture. In the preferred embodiment the shield is relatively thin, of substantially uniform wall thickness, and sufficiently resilient as permits the opposite sides of the outer periphery of the shield to be bendable into an overlying relationship to the handle portion, and to rebound to their relaxed state as a part of the shield. Further, the shield is preferably formed initially of a concave geometry such that the outer periphery of the shield drapes toward the closed end of the handle portion.

For purposes of minimizing space in the packaging and storage of the present disposable light handle, the shield is provided with open loop-type projections located diametrically opposed to one another on the outer periphery of the shield. The handle portion is provided with projections at locations along the length of the handle portion and disposed on opposite sides of the handle in position to releasably receive thereon the open loop-type projections of the shield when the shield is bent to position its opposite sides in overlying relationship to the handle portion.

As a further aspect of the present invention, provision is made for the interconnection of two light handles in a single package. This feature is accomplished in the preferred embodiment by providing an elongated groove in the closed end of the handle portion of a first light handle, the groove opening outwardly both from the side surface and of the distal surface of the closed end of the handle portion. On the same side of the first light handle as the location of its elongated groove, there is provided an elongated projection which is located at the junction of the handle portion and the shield. The projection extends away from the shield along a portion of the length of the handle portion in position to be received in the elongated groove of a second light handle. For packaging of first and second light handles in a single package, the closed end of the first light handle is positioned at the junction of the handle portion and shield of the second light handle such that the groove of the first light handle receives therein the projection of the second light handle and vice versa. This relative positioning of the two light handles further locates the closed end of the second light handle at the junction of the handle portion and shield of the first handle portion whereby the projection at the juncture of the handle portion and shield of the first light handle is received in the groove in the closed end of the second light handle thereby providing for two spaced apart interlocking locations of the first and second light handles. The elongated structure of these interlocking grooves and projections on the two light handles provides several advantages including ease of assembly and disassembly of the two light handles, and positive interlocking of the two light handles for handling during packaging operations and during removal of the two light handles under sterile conditions within a surgical suite such that the two light handles do not inadvertently separate during their removal from their packaging and are dropped outside the desired sterile field, for example.

In one embodiment, the junction between the handle portion and the shield is defined by a circular transition shoulder which is of greater thickness than the shield and provides strengthening of the interconnection of the shield to the handle portion. This enhanced strengthening of this juncture permits repeated flexing and enhanced resiliency of the shield relative to the handle portion as when bending the opposite sides of the shield into overlying relationship to the handle portion.

In an alternative embodiment, the light handle of the present invention is combined with an adaptor which receives the threaded portion of the light handle and a differently threaded or shaped receiver or receptacle on the light handle, thereby permitting the present light handle to be employed with differing existing light fixtures.

In an alternative embodiment, the handle portion of the present light handle is of a multi-sided cross-sectional geometry to aid in the sure grasping of the handle during its use. Further, the cross-sectional diameter of the handle portion preferably is varied from a first and smaller diameter nearest its closed end and a second and greater diameter commencing at the location of the projections thereon which receive the loop-type projections of the shield, and extending to the juncture of the handle portion and the shield. Employing these different diameters of the handle portion, the present invention provides for the orientation of the projections in a direction substantially parallel to the length of the handle portion. By this means, the projections are in position to readily receive and retain the loop-type projections of the shield, while also providing for the ready release of the loop-type projections from the projections on the handle when the present light handle is removed from its sterile packaging for use. Further, the placement and orientation of the projections on the handle minimizes their destruction or mutilation during handling and minimizes any likelihood that these projections will damage the glove of a user and thereby destroy the desired sterile field.

In an alternative embodiment, the disposable light handle includes an elongated body portion having an outer surface, a closed end and an opposite end adapted to be attached to a light fixture for manipulation of the light, and a generally circular shield extending radially from the body portion at a location adjacent the opposite end of the light handle. The light handle improvement comprises an elongated groove defined in the outer surface of the body portion, the groove originating at the closed end of the body portion and extending along a portion of the length of the body portion to terminate short of the shield, the groove having a cross-section having a perimeter which is continuous except for a single opening defined in the perimeter, the opening comprising less than one-half of the perimeter of the cross-section perimeter. The light handle improvement further comprises an elongated tongue projecting from the outer surface of the body portion at a location substantially opposite the location of the groove in the outer surface, the tongue originating adjacent the closed end of the body portion and extending along at least a portion of the length of the body portion, the tongue having a cross-section having a closed perimeter which is complementary to the cross-section of the groove, whereby the tongue is receivable within the groove to releasably interconnect a first light handle to a second light handle of like design.

BRIEF DESCRIPTION OF DRAWINGS

The above mentioned objects and advantages of the present invention are readily apparent from the description contained herein, and by reference to the claims, read together with the drawings in which:

DETAILED DESCRIPTION OF INVENTION

An improved disposable light handle 10 incorporating various features of the present invention is disclosed and illustrated generally in FIGS. 1–12. The disposable light handle 10 can be compactly packaged for space-efficient and steril-estorage until utilized in sterile medical environments, and can be easily unpackaged and assembled by sterile-gloved medical personnel in surgical suites, dental offices, and medical treatment rooms. The light handle 10 can be sterilized and attached directly to an existing threaded attachment means, such as a threaded female receptacle, on a manually adjustable light fixture 77 (see FIG. 10). Alternatively, an adaptor A (see FIG. 12) can be attached to the light handle 10 for connecting the light handle 10 to a light fixture 77 having a different diameter than the light handle 10. The disposable light handle 10 allows medical and dental users in sterile operating rooms to grasp and adjust the light fixture 77 without destroying the sterile conditions of the user's gloved hands.

Figure 10:
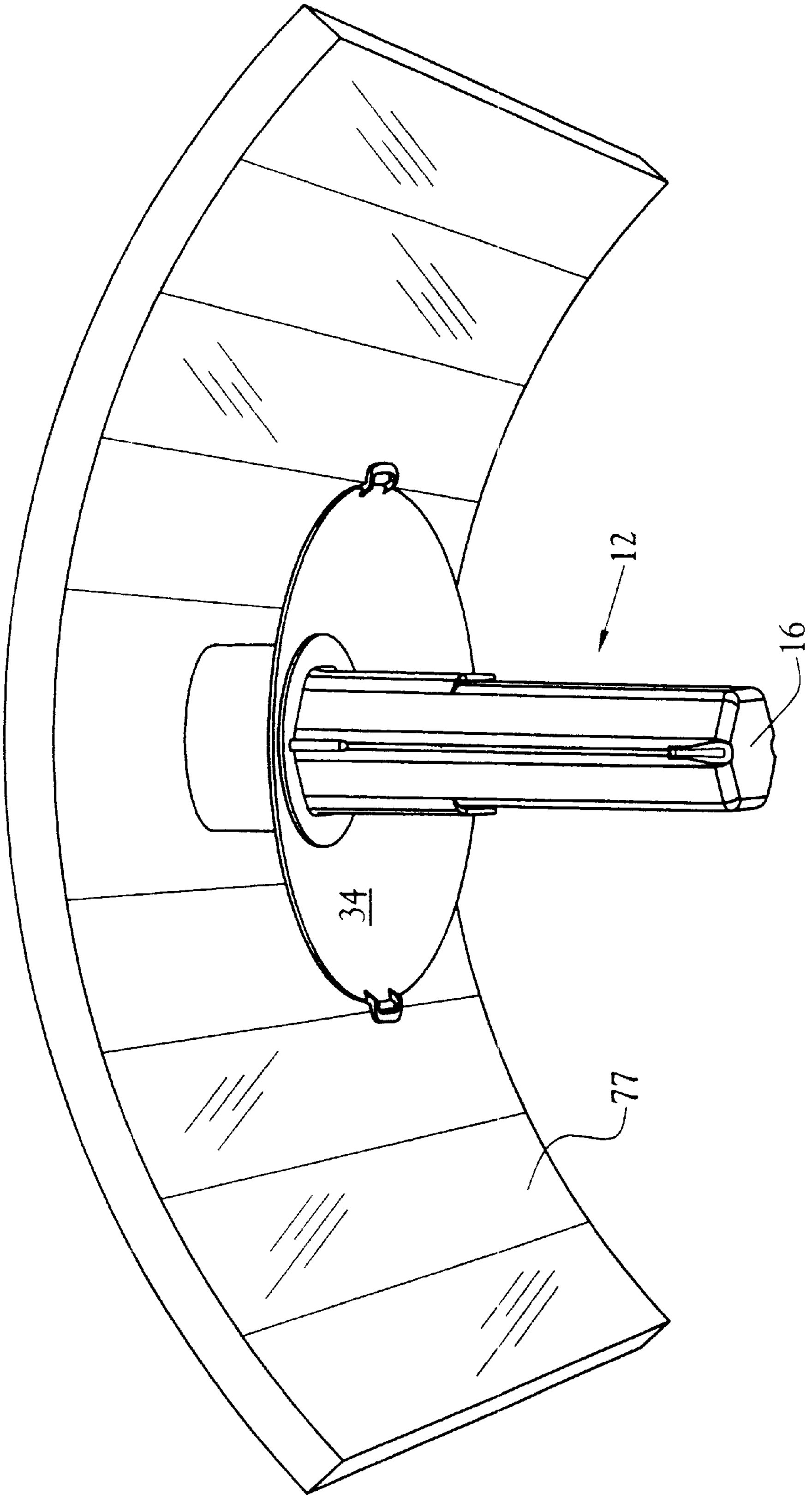
FIG. 10 is a perspective view of the light handle connected to a light fixture.

One embodiment of the light handle 10 comprises a handle body portion 12 of a generally elongated, hollow, cylindrical shape with a first end 14 defining a closed end 16 (see FIG. 1) projecting downward or toward the medical treatment area when the handle is removably attached to an existing threaded attachment means on a light fixture 77 (see FIG. 10). The exterior surfaces 18 of the first end 14 may be formed as a smoothly curved or ribbed outer surface, or a multi-sided exterior shape with a plurality of outer surface portions 20 of generally equal width. A preferred multi-sided shape may include hexagonal or octagonal shaped outer surface portions 20 that may have equal widths for each exterior surface portion 18. The multi-sided handle body 12 allows medical personnel who are wearing sterile and possibly wet gloves to easily grab and maintain a grip on the handle body 12 to quickly reposition the light fixture 77 during a surgical procedure.

In a preferred embodiment there is provided an increase from a first diameter of the handle body 12 at the closed end 14, to a second diameter 24 at a generally central junction 22 along the length of the handle body 12. The depicted junction 22 (see FIGS. 2 and 3) includes a bevel of transition 26 at the junction from the lesser diameter of the first end 14, to the increased second diameter 24 of the handle body 12. The second diameter 24 preferably extends distally from the junction 22 toward the second end 28 of the handle body 12.

An open second end 28 of the handle body 12, opposite the first end 14, is provided with a threaded portion 36, or spiral groove. The threaded portion 36 preferably includes external threads 37 (see FIGS. 1 and 2). The threaded portion 36 preferably is integral with the handle body 12 at approximately a shield junction 30 on the handle body 12 that is distal to the generally central junction 22.

At the shield junction 30, there is provided a generally circular shield 34, that is integrally formed with the handle body 12 at the shield junction 30, and extends radially from the handle body 12. The shield 34 projects outward from the handle body 12 to provide a guard against contact between the hand of a user and non-sterile areas of a light fixture 77 during attachment of the handle 10 to the light fixture 77 (see FIG. 10), and during grasping of handle 10 by the user during manual adjustment of the light fixture 77.

In the preferred embodiment, the shield 34 is relatively thin, of substantially uniform wall thickness, and sufficiently flexible and resilient to permit the opposite sides of the outer periphery 38 of the shield to be bent into an overlying relationship to the handle body 12 (see FIG. 3), and for the shield to reassume its relaxed position when released from its bent state. Further, the shield is preferably formed initially of a concave shape such that the outer periphery 38 of the shield drapes toward the closed end 16 of the handle body 12. The concave geometry of the shield 34 enhances the inherent resiliency of the shield in that bending of diametrically opposite sides of the shield toward the handle body 12 so deforms the circular geometry of the shield as to increase its tendency to return to its concave geometry when released from its bent state. In effect, the bending of the concave shield 34 stores more energy in the shield than does the bending of a planar shield.

In one embodiment, the shield junction 30 between the handle body 12 and the shield 34 is defined by a circular transition shoulder 32 that is of greater thickness than the shield 34, and which extends radially from the handle body by a relatively short distance, approximately one quarter inch, for example. The shoulder 32 provides for a strengthening of the interconnection of the shield 34 to the handle body 12, and permits repeated flexing of the shield 34 relative to the handle body 12 as when bending the shield 34 into overlying relationship to the handle body 12 for packaging purposes, or extending the shield for use when the handle body is attached to a light fixture 77.

As noted above and shown in FIGS. 3 and 11, the shield 34 of the present invention may be resiliently bent into overlying relationship toward the outer surface 20 of the handle body 12, and releasably secured in their bent positions. The present invention employs this feature for purposes of minimizing space in the packaging and storage of the present disposable light handle 10. To this end, the shield 34 is provided with first and second attachment means such as open loop-type projections 64, 66 located diametrically opposed to one another on the outer periphery 38 of the shield 34 (see FIGS. 5, 6 and 8). The handle body 12 is provided with first and second connector means such as connector projections 50, 50' at locations at approximately a mid-length distance along the length of the handle body 12 and disposed on opposite sides of the handle body 12 in position to releasably receive thereon the open loop-type projections 64 when the shield 34 is bent to position its opposite sides in overlying relationship to the handle body 12. In a preferred embodiment, the open loop-type projections on the shield 34 comprise a first loop projection 64, and a second loop projection 66 disposed on diametrically opposite sides of the periphery 38 of the handle body 12 (see FIG. 4).

Figure 1:
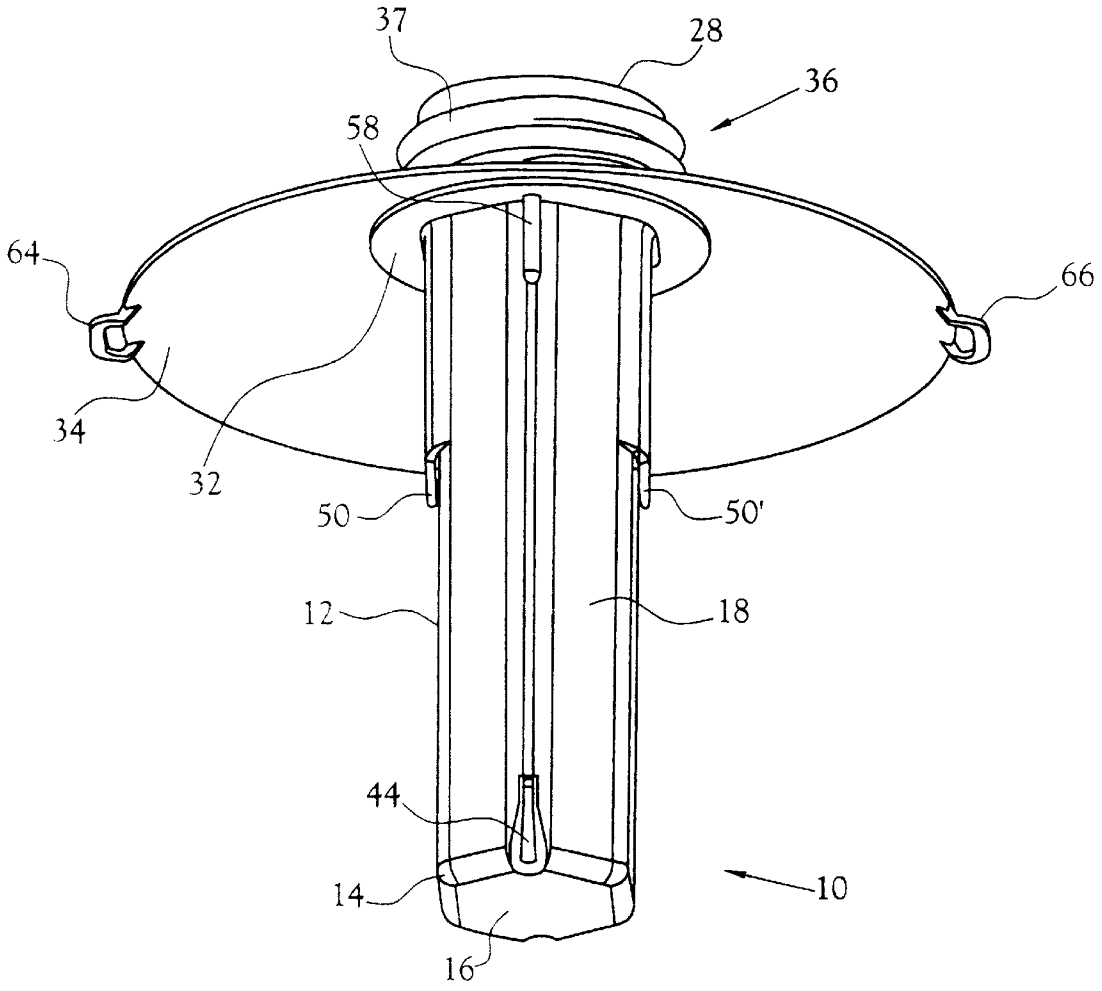
FIG. 1 is a perspective view of one embodiment of a disposable light handle in accordance with the present invention.
Figure 3:
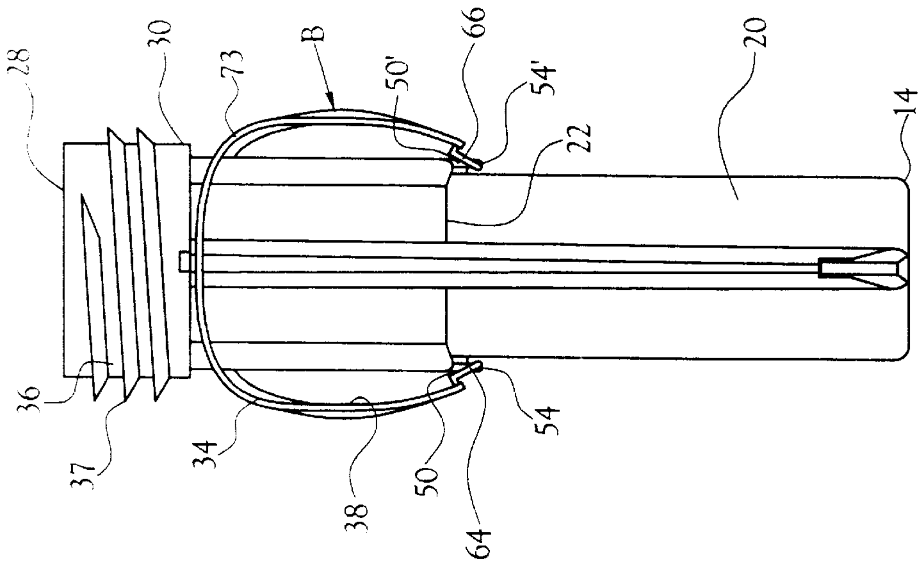
FIG. 3 is a side view of FIG. 2, rotated ninety degrees, illustrating at least two loop-type projections originating on the periphery of the shield, with each loop-type projection connected to a connector positioned at the junction of the different diameters of the handle portion.
Figure 7:
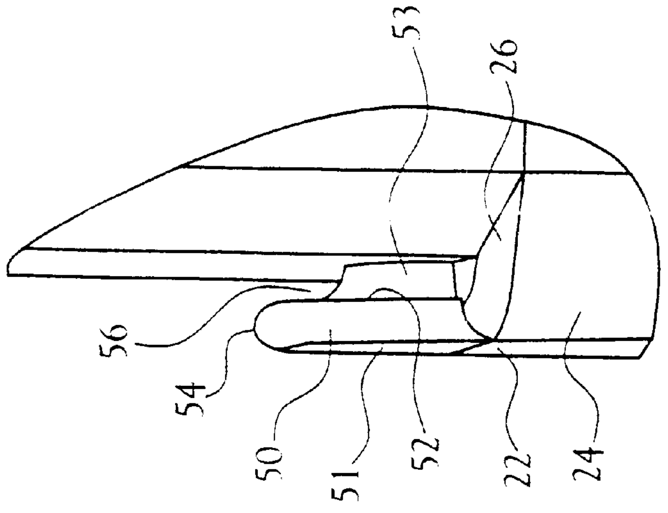
FIG. 7 is a detailed view of a connector projection extending toward the first end of the handle body of the present invention.
Figure 6:
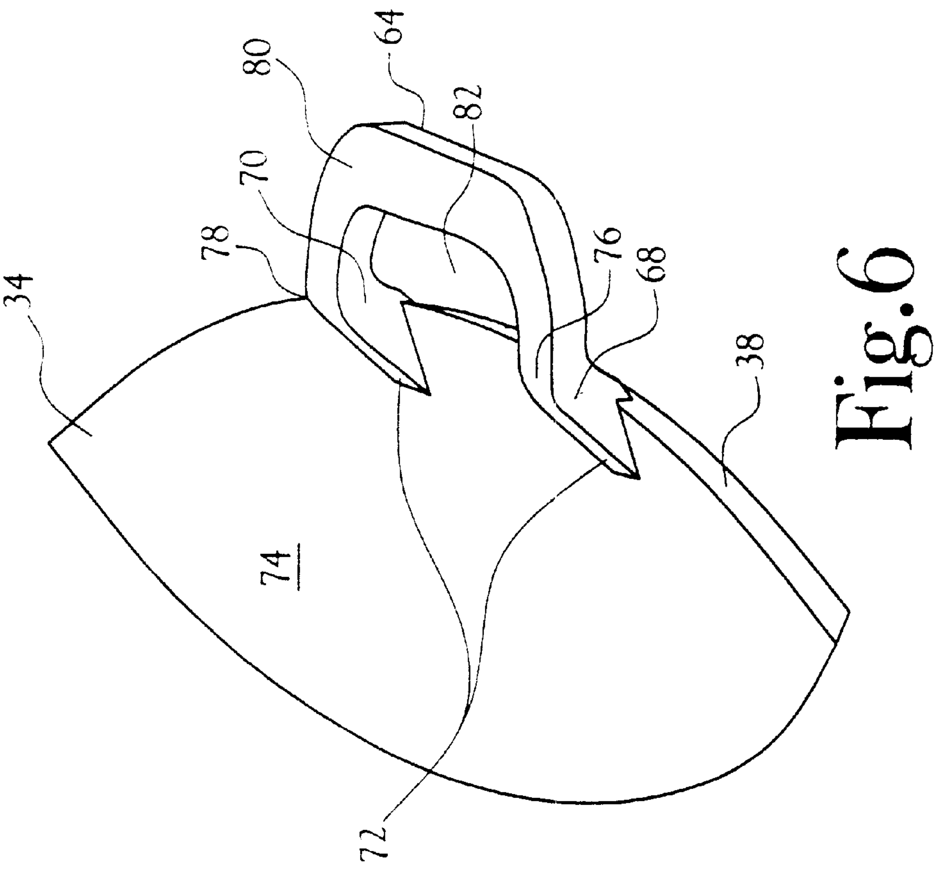
FIG. 6 is a detailed view of a loop on the periphery edge of the circular shield.
Figure 9:
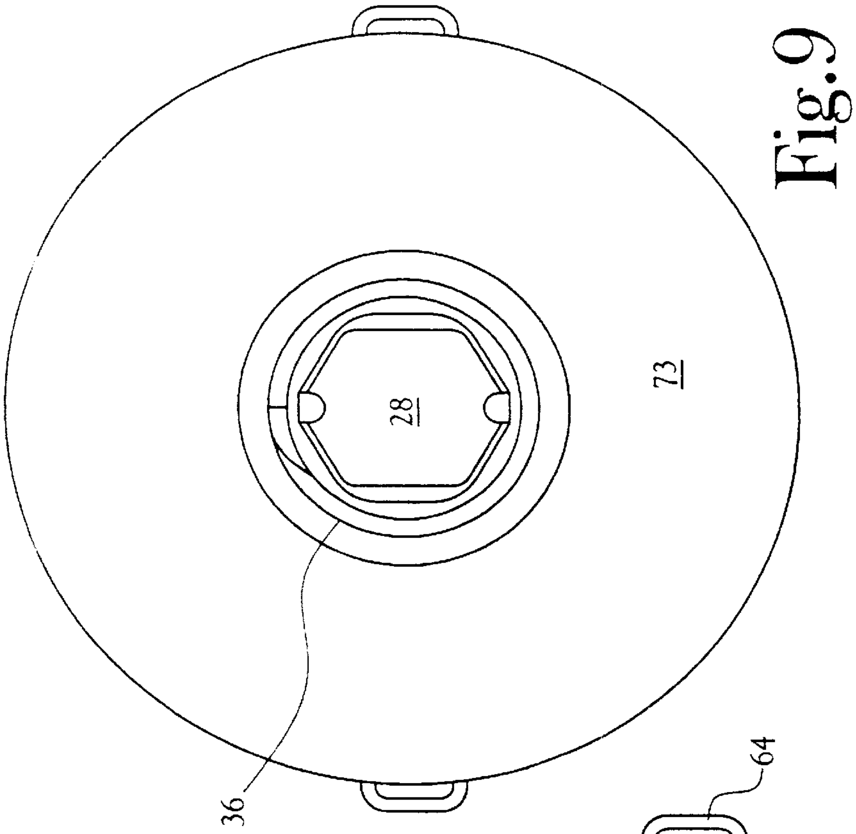
FIG. 9 is a top view of the second open end of the handle body.
Figure 8:
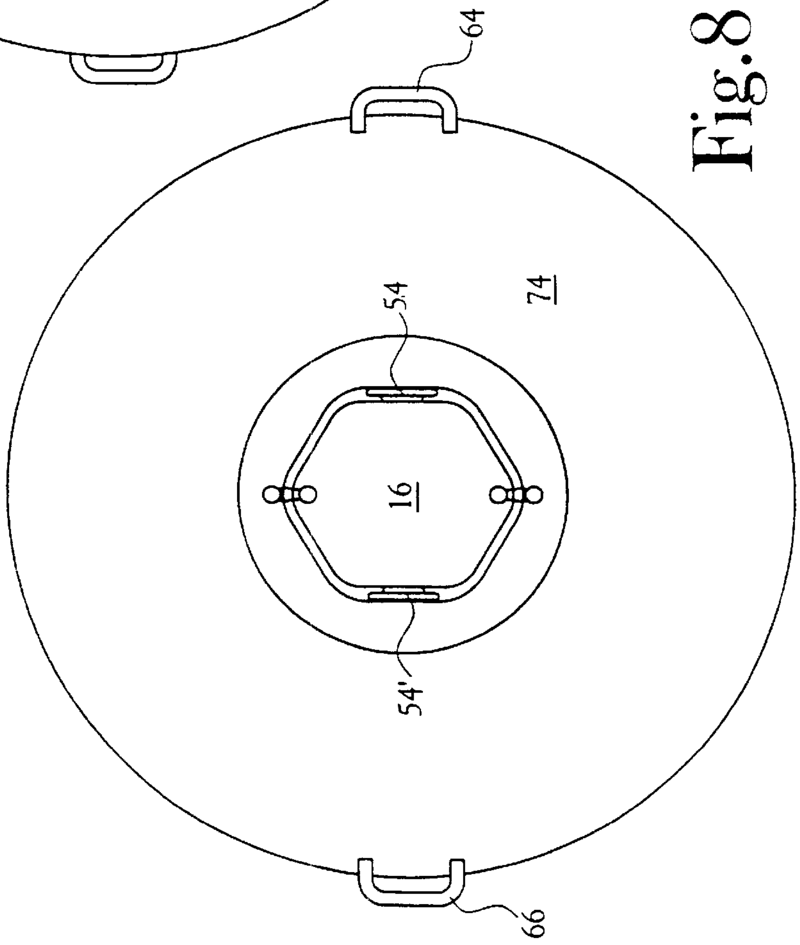
FIG. 8 is a bottom view of the first end of the handle body.

Referring to FIGS. 3, 6 and 7, to maintain the opposite bent sides of the shield 34 in their overlying positions with respect to the handle body 12, the handle body is provided with first and second connector projections 50, 50', each of which projects from the other surface 20 of the handle body 12, toward the closed end 16. Each connector projection 50, 50' is in position to receive one of the loop-type projections 64, 66 on periphery 38 of shield 34.

Figure 2:
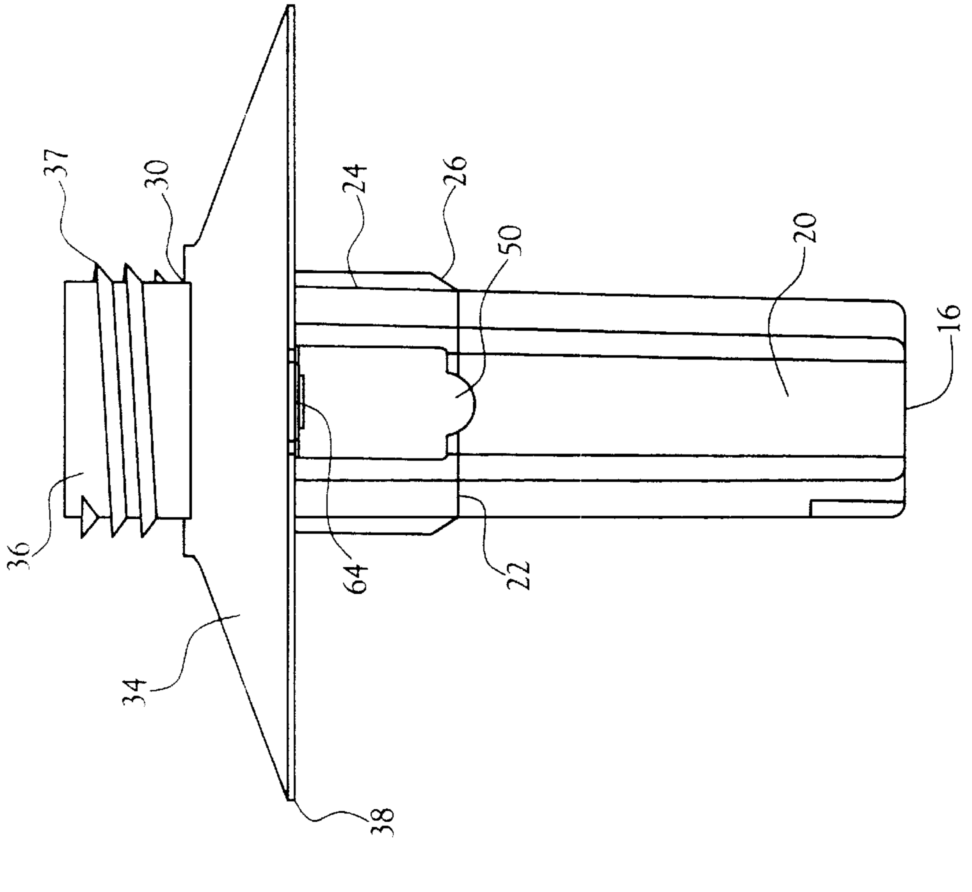
FIG. 2 is a front view of the light handle of FIG. 1, illustrating a circular shield connected at a junction of the handle portion of the handle with a threaded portion.

In FIGS. 2, 3 and 7, each of the connector projections 50, 50' comprise a flat planar body portion 51, 51' and a distal end having a generally arcuate tip 54, 54'. The inboard edge 52, 52' of each connector is integrally formed with the bevel 26 defined at the bevel of transition 26 on the handle body 12 such that the flat planar body portion 51, 51' of the connector projections 50, 50' have outboard ends that lie substantially parallel with, but spaced apart from the handle body 12 to define a slot 56 between each connector projection 50, 50' and the handle body 12. This slot 56 opens outwardly in a direction toward the closed end 16 of the handle body 12, hence in a direction away from the shield 34. Each slot 56 is dimensioned to accept therein one of the loop-type projections 64, 66 on the periphery 38 of the shield 34.

Figure 4:
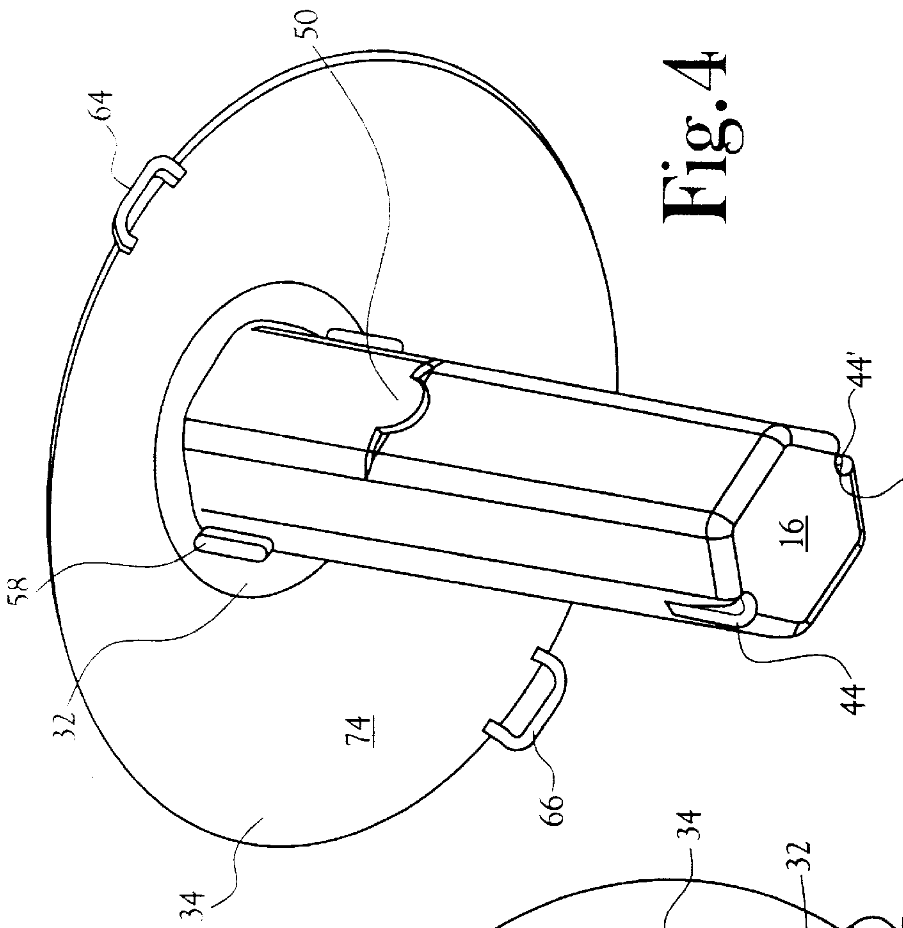
FIG. 4 is a bottom perspective view of the light handle of FIG. 1, illustrating at least two grooves in the first end of the handle body, plus at least one insert projection on the handle body aligned with one of the grooves in the first end.
Figure 5:
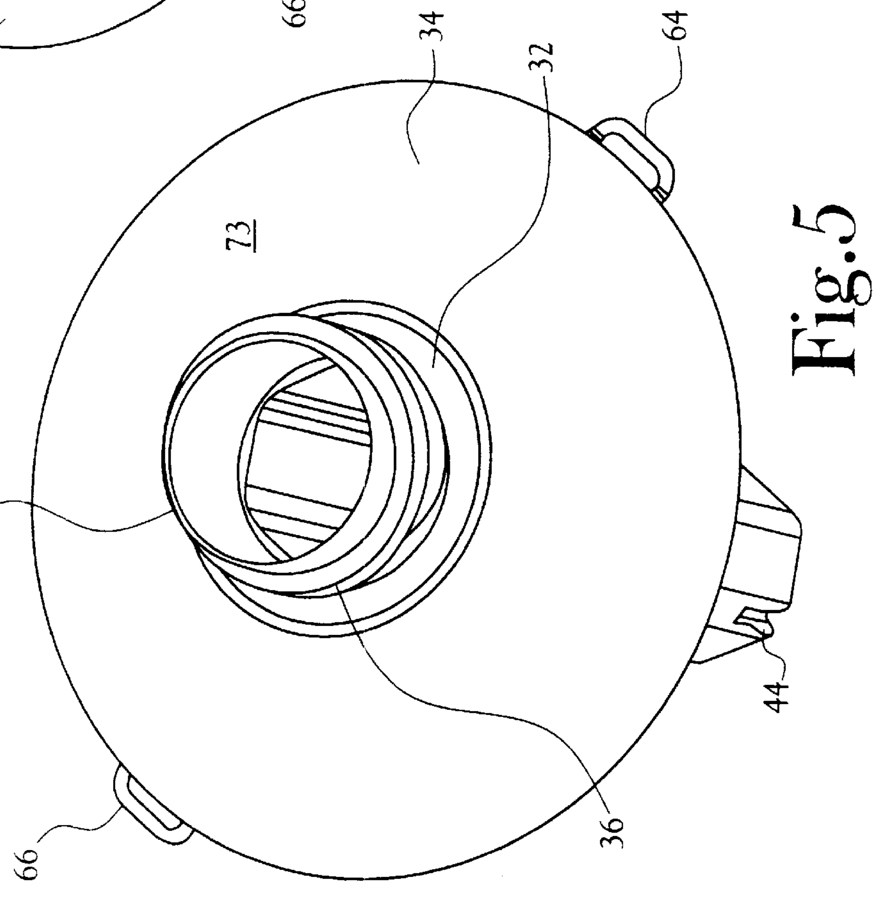
FIG. 5 is a top perspective view of FIG. 4.

In the depicted embodiment of FIGS. 4 and 5, each of the loop-type projections 64, 66 is of rigid or semi-rigid construction and includes first and second legs 68, 70, respectively (see FIG. 6). One end 72 of each leg is integrally formed with and extends from the periphery 38 of the shield in an angled direction away from the lower surface 74 of the shield facing the closed end 16. The outboard ends 76, 78 of the legs are joined by a generally U-shaped cross member 80 which is integrally formed with the legs to define an opening 82. Notably, the orientation of the U-shaped cross member 80 of each loop-type projection 64, 66 lies in a plane which is generally parallel to, but spaced apart from the surface 74 of the shield 34. Thus, when the periphery 38 of the shield 34 is bent into a position in which the shield overlies the handle body 12, toward the closed end 16, the plane of the U-shaped cross member 80 of the loop-type connector is oriented substantially parallel to the outer surface 20 of the handle body 12. Further, when in this position adjacent the handle body, the U-shaped cross member 80 is disposed to readily enter the slot 56 defined by a connector projection 50, 50' on the handle body 12. To provide for entry of the U-shaped cross member 80 into the slot 56 defined by each connector projection 50, 50', the location of each connector projection 50, 50' along the length of the handle body 12 is selected to cause the connector projection (and its slot) to be disposed away from the shield junction 30 by a distance which places the opening of the slot 56 immediately adjacent to the location of the U-shaped cross member 80 of each loop-type projection 64, 66 of the shield 34. Thus, when the shield is bent into substantially complete overlying position with respect to the handle body 12, the U-shaped cross member 80 is presented to the open end of the slot 56 for ready entry into the slot. Notably, the angularity of the mounting of the U-shaped cross member 80 with respect legs 68, 70 connected to the surface 74 of the shield 34, in concert with the slight angle of the legs away from the general plane of the shield 34 toward the first end 14, positions the periphery 38 of the shield in spaced apart relationship to each projection connector 50, 50' on the handle body 12, thereby precluding the surface 74 of the shield 34 from interfering with entry of each cross member 80, 80' into each slot 56, 56'.

However, it is to be noted that the connection of each loop-type connector 50, 50' to the shield 34 is of a resilient nature so that the application of a force against the upper surface 73 of the shield adjacent the location of the loop-type connectors 64, 66, functions to bend the shield 34 loop-type connectors 64, 66 toward the outer surface 20 of the handle body 12. Continued force against the upper surface 73 of the shield urges each U-shaped cross member 80 into substantial parallel and close proximity with the outer surface 20, hence positioning only the cross member 80 in actual engagement with the outer surface 20 of the handle body 12 and in position adjacent the open end of the slot 56. Once the shield

12 has been bent into substantially complete overlying relationship to the outer surface 20 of the handle body 12 and upon release of a force employed to resiliently bend the shield 34 into its overlying position with respect to the handle body 12, the resiliency of the shield 34 functions to urge each U-shaped cross member 80, 80' in a direction toward the handle body/shield shoulder 32, and hence into each slot 56, 56' and to lock each U-shaped cross member 80, 80' in each slot until the shield is again bent to the extent that the U-shaped cross member is urged away from and out of the slot. In this respect, release of the U-shaped cross member from the slot is readily accomplished by merely applying a force toward the closed end 16 against the outer surface 73 of the bent shield at a location intermediate the periphery of the shield and the shield juncture 30 to the handle body 12. Once each U-shaped cross member 80, 80' has been released from each respective slot 56, 56', release of all applied bending force against the shield 34 permits the shield to resiliently return to its concave geometry as desired when applying the handle 10 to a light fixture 77 and when grasping the handle 10 for adjustment of the position of a light fixture 77. Noting that the preferred embodiment includes first and second diametrically opposed projection connectors on the handle body 12 and first and second diametrically opposed loop-type connectors 64, 66 on the periphery 38 of the shield 34, a user may effect bending of both sides of the shield and locking of the loop-type connectors 64, 66 of the shield in their respective slots 56, 56' by merely grasping the shield between the thumb and forefinger of the user and squeezing the shield to position the loop-type connectors 64, 66 in their respective positions for engagement, and to effect the engagement upon release of the bent shield 34 (see FIG. 3). Disengagement of the sides of the shield from the handle body is performed in like manner, but with the bending force being applied to different locations on the bent shield (see arrow B of FIG. 3).

As a further aspect of the present invention, provision is made for the interconnection of two disposable light handles (see FIG. 11) in a single package for compact storage and shipping. This feature is accomplished in the preferred embodiment by providing at least one elongated groove 44, and preferably two opposed, elongated grooves 44, 44', in the closed first end 14 of the handle body 12 of a first light handle (see FIGS. 1 and 4). Each elongated groove 44, 44' opens outwardly both from an outer surface 20, and of the closed surface 16 of the first end 14 of the handle body 12. On the same side of the first handle body 12 as the location of the first elongated groove 44, there is provided an elongated, insert projection 58 which is located at the shield junction 30 of the handle body 12 and the shield 34. The insert projection 58 extends along a portion of the length of the handle body 12, extending toward the closed end 16, and in an aligned position with the first elongated groove 44, of the first handle body 12, to receive therein the elongated groove 44' of a second light handle (see FIG. 11).

Figure 11:
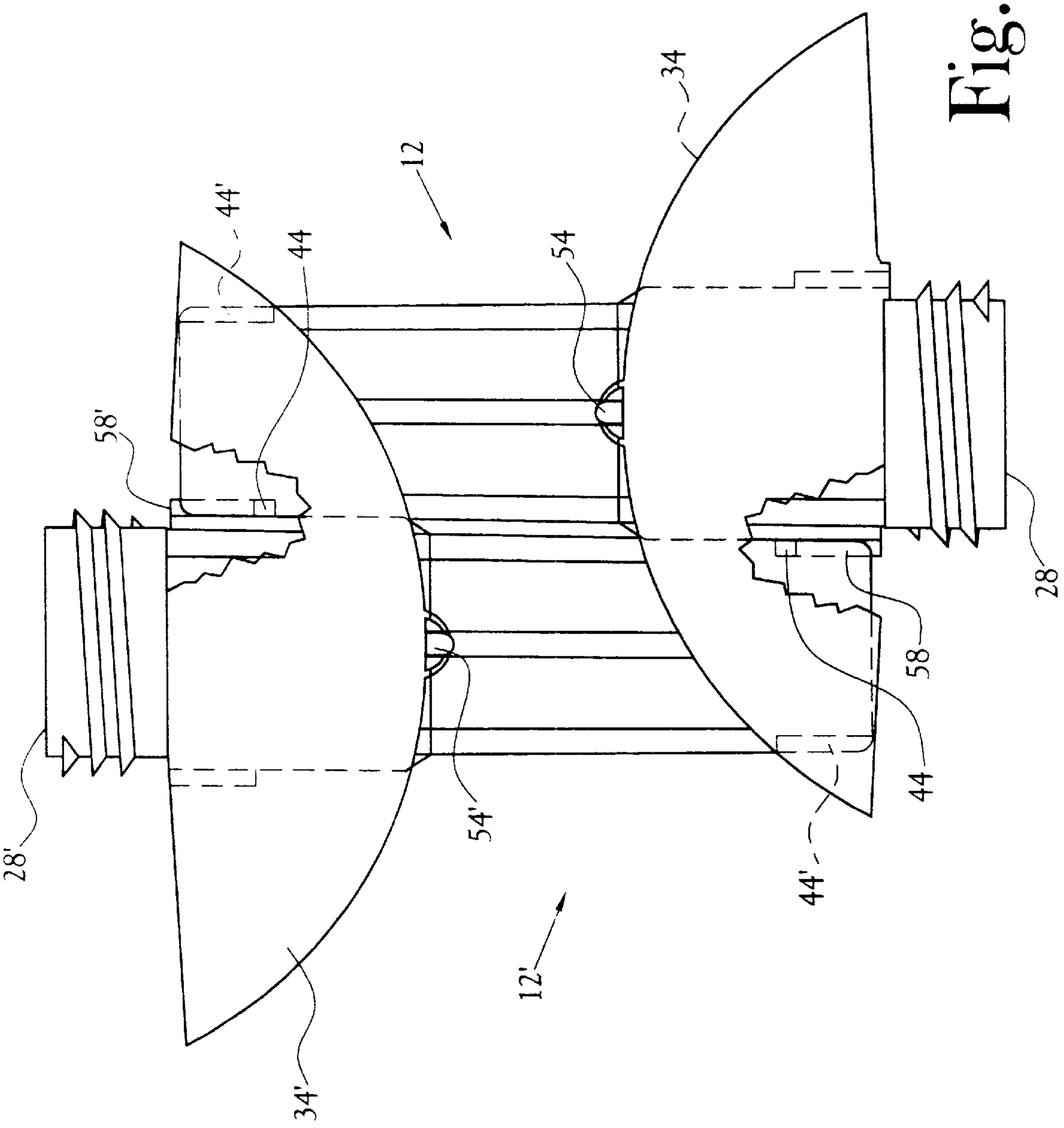
FIG. 11 is a perspective view of a first handle body attached to a second handle body, with each shield bent to a position in overlying relationship to each handle body.
Figure 12:
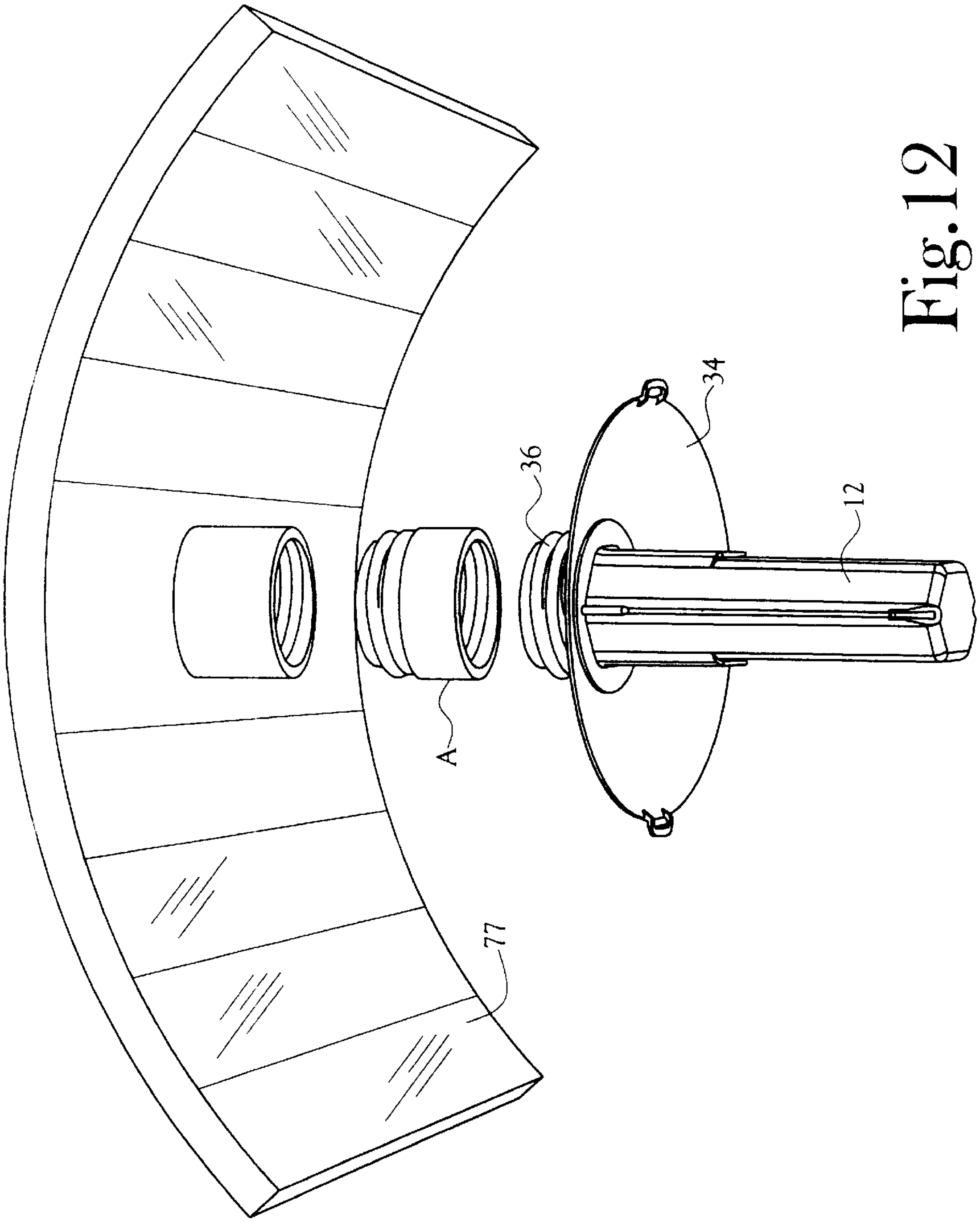
FIG. 12 is a perspective view of the light handle and an adaptor connected to a light fixture.

For packaging of first and second light handles in a single package, the closed end 16 of the first light handle 10 is positioned near the shield shoulder 32 of the shield 34' of the second handle body 12', such that the groove 44 of the first light handle 12 receives therein the insert projection 58' of the second handle body 12', (see FIG. 11). This relative positioning of the two light handles of like design further locates the closed end 16' of the second handle body 12', near the shield shoulder 32 of the shield 34 of the first handle body 12. Concurrent with insertion of the second handle body 12' insert projection 58' into the groove 44 of the first handle, the insert projection 58 of the first handle body 12 is received in the groove 44' in the closed end 16' of the second handle body 12', thereby providing for two spaced apart interlocking locations of the first and second light handles. The elongated structures of the interlocking grooves 44, 44' and insert projections 58, 58' on the two light handle bodies provide several advantages. One advantage includes ease of assembly and disassembly of the two light handles as each respective insert projection inserts into the elongated grooves 44, 44'. Another advantage includes positive interlocking of the two light handles to maintain interlocked orientation during transport and removal of light handles under sterile conditions within a surgical room, such that the two light handles do not inadvertently separate during their removal from packaging and are dropped outside the desired sterile field, for example. A further advantage includes positive interlocking of the two light handles so that one handle does not rotate in relation to the other light handle during transport and/or during removal from packaging of the handles.

The open second end 28 of the handle body 12 includes a threaded portion 36 having external threads 37 or internal threads (not shown). This threaded portion 36 can be screwed directly onto a light fixture 77, or can be combined with an adaptor A (see FIG. 12) which receives the threaded portion 36 of the second end 28 and connects to a differently threaded or shaped receiver or receptacle on the light fixture 77, thereby permitting the present handle body 12 to be employed with different configurations of existing light fixtures.

Alternative embodiments for interlocking of a first handle body to a second handle body are illustrated in FIGS. 13–17 as a tongue and groove releasably interlocking means. One alternative embodiment comprises a light handle body 112 including a multi-sided outer surface 114 having a outboard closed end 116, a first side 118, a second side 120 substantially diametrically opposed to the first side 118. The first side 118 includes a first connector projection 142 located at a distance along the length of the first side 118 toward the second open end 128. The second side 120 includes a second connector projection 144 located at a distance along the length of the second side 120 toward the second open end 128 and approximately opposite the location of the first connector projection (see FIGS. 13*a*, 13*b* and 14). A third side 122 is oriented between the first side 118 and the second side 120, and a fourth side 124 is substantially diametrically opposed to the third side 122. The handle body 112 may be tubular with four or more sides, or cylindrical or oval in cross-section with the connector projection means located on opposing sides of the perimeter of the cylindrical or oval handle body (not shown). An alternative embodiment provides a shield having a multi-sided shape, such as a hexagon (not shown), or an octagon 134' (see FIG. 13*b*), or a generally square shape 134" (see FIG. 14), with any of the cross-sectional shapes for the handle body 112 as stated above.

Figure 13A:
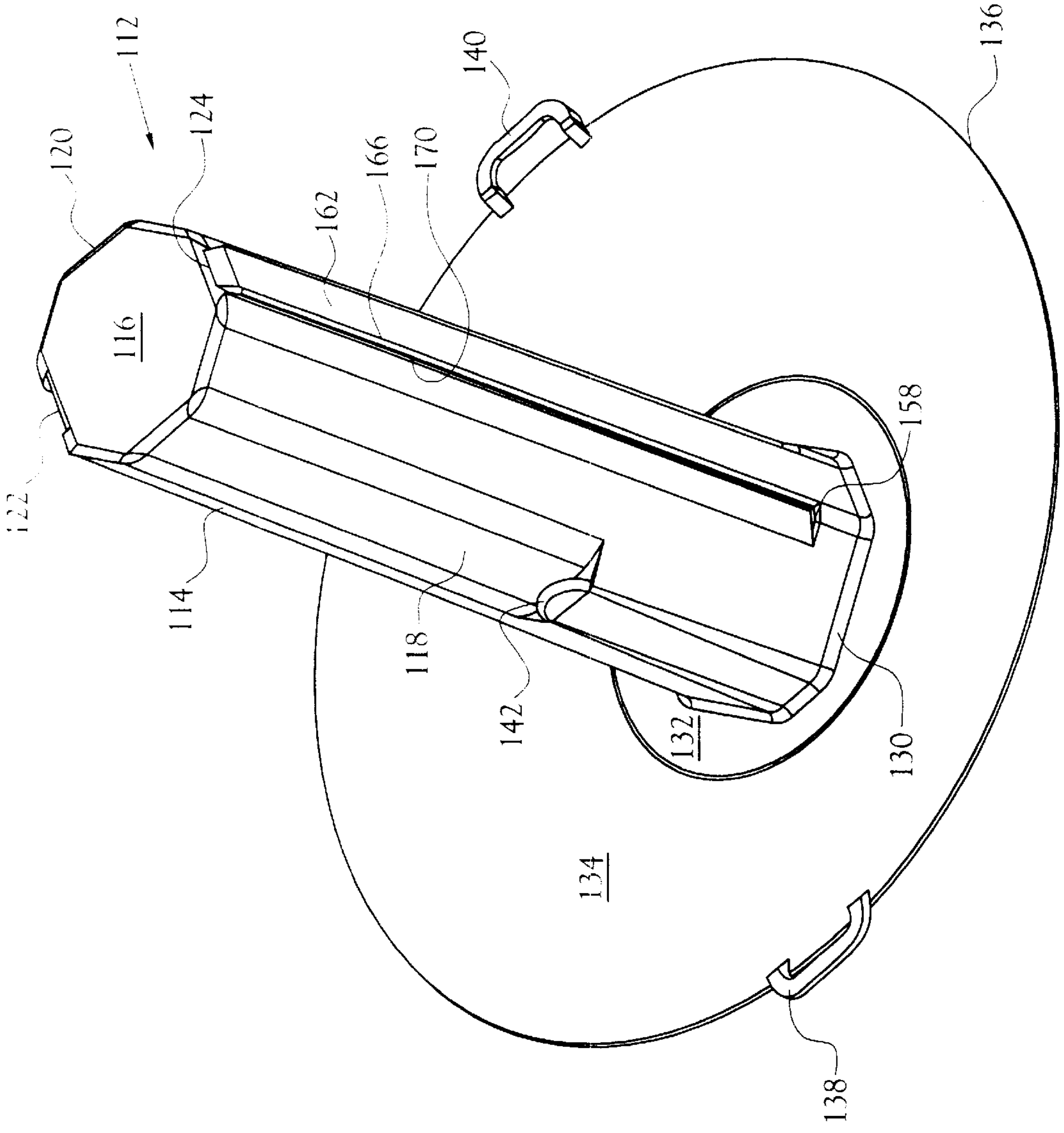
FIG. 13*a* is a perspective view of an alternative embodiment of the light handle.
Figure 13B:
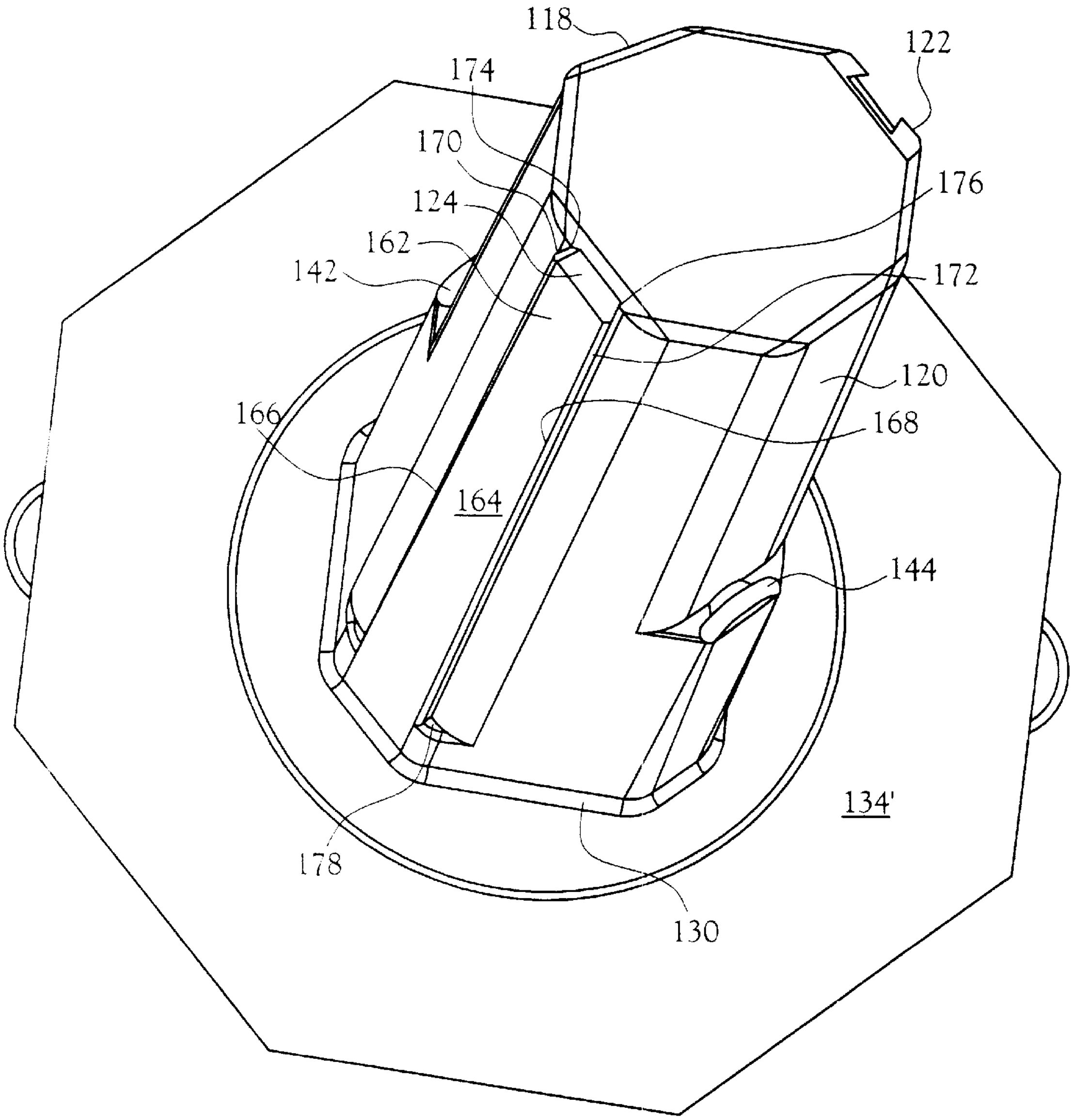
FIG. 13*b* is a perspective view of FIG. 13*a* illustrating details of a tongue and groove interlocking means on the handle body having an alternative shaped shield.
Figure 14:
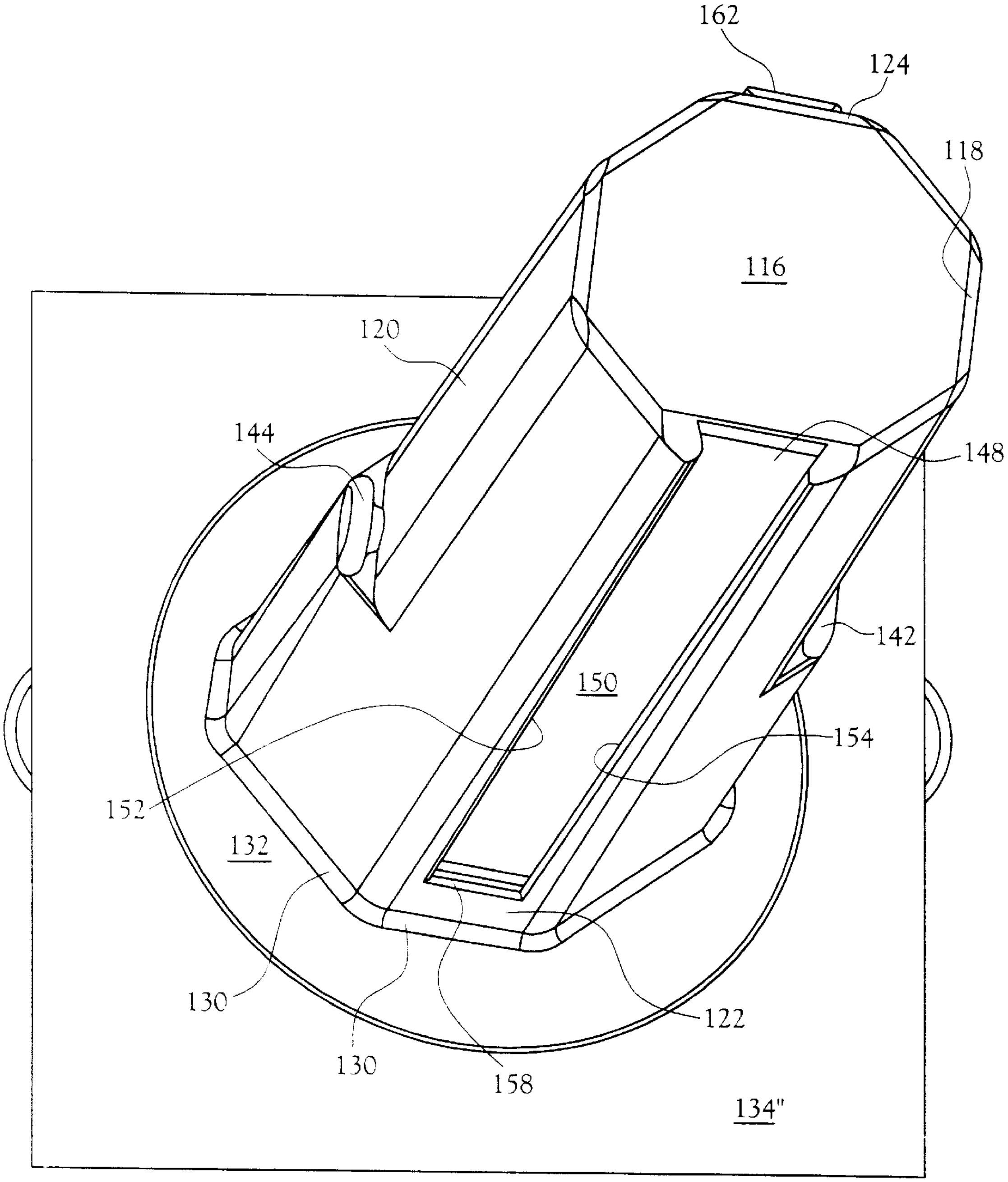
FIG. 14 is a perspective view of an opposite side of the embodiment of FIG. 13*a* illustrating the handle body having an alternative shaped shield.

In one embodiment, a generally circular shield 134 is integrally formed with the handle body 112 proximate the open end 128, with the central portion of the shield 134 having a shoulder 132 that is connected to a bevel 130 against the outer surface 114 of the handle body 112 (see FIG. 13*a*). The shield 134 extends generally radially from the handle body 112, and includes an outer periphery 136 of substantially uniform thickness over its area. The shield 134 is sufficiently resiliently flexible to permit diametrically opposed portions of the periphery 136 to be bent into overlying relationship to the handle body 112. The periphery 136 includes first and second attachment means comprising a first loop 138 and a second loop 140 that are disposed at substantially diametrically opposed locations on the shield 134. The first loop 138 is positioned on the periphery 136 to align with, and connect onto, the first connector projection 142, and the second loop 140 is positioned on the periphery 136 to align with, and connect onto, the second connector projection 144. The positions of the first connector projection 142 and second connector projection 144 are spaced along the length of the handle body 112 at a distance from the second open end 128 suitable for releasable engagement of the first loop 138 and second loop 140 on the shield with respective first 142 and second 144 connector projections to allow the flexible shield to be bent into overlying relationship and connected to the handle body 112 for compact storage and packaging.

The tongue and groove connection means of the depicted alternative embodiment for the handle body 112 includes an elongated groove 148 disposed in the third side 122 of the outer surface 114. The groove 148 opens outwardly of the handle body 112, With the groove 148 originating at, and opening outwardly of, the outboard closed end 116 and extending along a portion of the length of the third side 122, ending at a ledge 158 that is located in spaced apart relationship to the shield 134. The groove 148 includes a bottom wall 150 disposed inwardly of the outer surface 114, and opposite side walls 152, 154 which extend outwardly from the bottom wall 150, toward the outer surface 114, to form angled side walls 152, 154 that have an opening width between the outer edges of the side walls 152, 154 that is less than the width of the bottom wall 150.

The tongue and groove interlocking means further includes an elongated tongue 162 projecting from the fourth opposing side 124 of the outer surface 114. The tongue 162 extends from the outboard closed 116 along a portion of the length of the fourth side 124 and ends at a ledge stop 178 spaced apart from the bevel 130 and shoulder 132 of the shield 134. The tongue 162 includes an outboard surface 164 which includes opposite side edges 166, 168 which extend along substantially the length of the tongue 162, and includes opposite side walls 170, 172 which extend from the opposite side edges 166, 168 and join the outboard surface 164 to the handle body 112. The side walls 170, 172 diverge from one another from their respective joinder locations 174, 176 with the outer surface 114 of handle body 112, to their respective joinder locations with the opposite side edges 166, 168 of the tongue 162, whereby a tongue of a first light handle is receivable within a groove of a second light handle of like design to thereby releasably interconnect the first and second light handles to one another.

Figure 17:
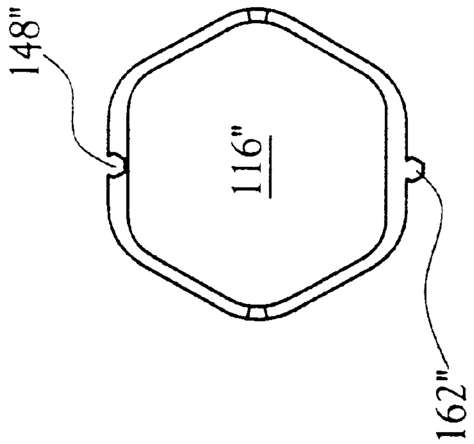
FIG. 17 is an alternative embodiment of FIG. 14 of the present invention.
Figure 16:
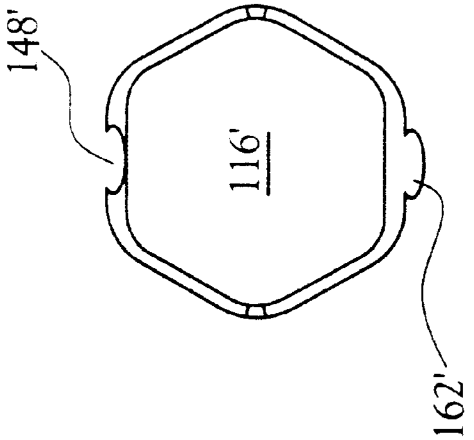
FIG. 16 is an alternative embodiment of FIG. 14.
Figure 15:
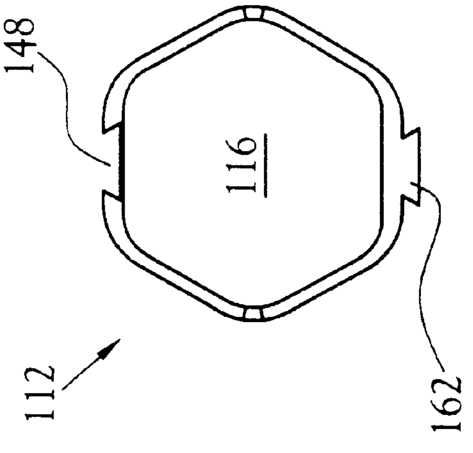
FIG. 15 is a cross-section of one embodiment of a groove of FIG. 14.

Alternative cross-sections of the tongue and groove interlocking means are shown in FIGS. 15–17, viewed from the outboard closed end 116. In FIG. 15, the cross-section of the tongue 162 and groove 148 having angled side walls is illustrated. In FIG. 16, the tongue 162' and groove 148' having complementary circular cross-sections is illustrated. In FIG. 17, the tongue 162" and groove 148" having complementary hexagonal cross-sections is illustrated. With the cross-section of the tongue of a first handle body complementary to the cross-section of a groove of a second handle body of like design, the tongue is receivable within the groove of the second handle body to thereby releasably interconnect the first and second light handles to one another.

While a preferred embodiment is shown and described, it will be understood that it is not intended to limit the disclosure, but rather it is intended to include all modifications and alternative methods falling within the spirit and scope of the invention as defined in the appended claims. One skilled in the art will recognize variations and associated alternative embodiments. The foregoing description should not be limited to the description of the embodiment of the invention contained herein.

What is claimed is:

1. A disposable light handle for a manually adjustable light fixture of the type employed in medical treatment and operating rooms, said light handle comprising:

an elongated handle body portion having an outer surface and first and second opposite ends, a generally circular shield integrally formed with said handle body portion and extending generally radially from said handle body portion, said shield having an outer periphery and being relatively thin and of substantially uniform thickness over its area, and being sufficiently resiliently flexible as permits diametrically opposed portions of said periphery to be bent into overlying relationship to said handle body portion, first and second attachment means disposed on said periphery of said shield at substantially diametrically opposed locations, and first and second connector means disposed at respective substantially diametrically opposed locations on said outer surface of said handle body portion and spaced along the length of said handle body portion a distance suitable for releasably engagement of said first and second attachment means on said shield with respective ones of said first and second connector means disposed on said handle body portion.

2. The disposable light handle of claim 1, wherein the resiliency of said bent sides of said shield serves to retain said first and second attachment means on said shield in releasably engagement with said first and second connector means on said handle body portion.

3. The disposable light handle of claim 2, wherein the resiliency of said bent sides of said shield serves to return said bent sides to their relaxed state of radial orientation relative to said handle body portion, with said shield projecting outward in a concave geometry from said handle body portion such that said outer periphery drapes toward said first end.

4. The disposable light handle of claim 3, wherein each of said first and second attachment means disposed on said periphery of said shield comprises an open loop, each open loop is of suitable shape to readily and releasably engage respectively each one of said first and second connector means on said outer surface of said handle body portion when said shield is bent into overlying relationship to said handle body portion.

5. The disposable light handle of claim 4, wherein each of said open loop attachment means comprises first and second legs, each leg having one of its ends integrally formed with said periphery of said shield and projecting therefrom, each leg having an outboard end integrally joined by a cross-member to define an opening to engage each of said connector means.

6. The disposable light handle of claim 5, wherein each of said first and second legs extends angularly away from the general plane of said shield and in a direction toward said first end of said handle body portion.

7. The disposable light handle of claim 6, wherein each of said first and second connector means disposed on said handle body portion comprises a substantially flat planar body portion having inboard and outboard ends, said inboard end being integrally formed with said handle body portion and said outboard end extending in cantilevered fashion from and substantially parallel with said outer surface of said handle body portion to define an open space between said planar body portion and said outer surface of said handle body portion.

8. The disposable light handle of claim 7, wherein said distance suitable for the releasably engagement of said first and second attachment means with said first and second connector means is approximately a mid-length distance along said outer surface between said first and second opposite ends of said handle body portion.

9. The disposable light handle of claim 8, wherein said outer surface of said handle body portion further comprises a multi-sided outer surface having a multi-sided cross-sectional geometry that varies in diameter from a first and smaller diameter nearest said first end, to a second and greater diameter commencing at said mid-length distance along said outer surface of said handle body portion.

10. The disposable light handle of claim 9, wherein said first end further comprises a closed end, said first end including an elongated groove, said groove originating at said first end and extending axially toward said second end along said outer surface of said handle body portion, said groove opens outwardly both from said outer surface of said handle body portion and from said first end.

11. The disposable light handle of claim 10, wherein said outer surface further comprises an insert projection on said outer surface, said insert projection extends along the axis of said handle body portion, said insert projection is aligned with said elongated groove, said insert projection having a proximal end and a distal end, said proximal end extends toward said first end, said proximal end is proportioned to fit into said elongated groove, and said distal end extends toward said second end of said handle body portion.

12. The disposable light handle of claim 11, wherein said handle body portion of a first light handle is interconnectable to a second light handle having a second handle body portion of like design when the shields of each of said first light handle and said second light handle are bent into respective overlying relationship to each handle body portion with said loops of the shields attached respectively to said connector projections of each handle body portion, said elongated groove of said first handle body portion accepts the respective insert projection of said second handle body portion when said second end of said second handle body portion is aligned to said first end of said first light handle, thereby providing for two spaced apart and interconnected light handles for purposes of minimizing space in the packaging and storage of the disposable light handles.

13. A disposable light handle for a user adjustable light fixture such as employed in sterile medical treatment and operating rooms, said light handle is removably attachable to an existing threaded attachment means on the light fixture, said light handle comprises:

a handle body, said handle body having an elongated generally cylindrical geometry and an exterior surface;

a first end;

a generally circular shield integrally formed with said handle body, said shield projecting outward from said handle body, said shield being sufficiently flexible to be resiliently bent toward said handle body;

an outer periphery of said circular shield, said shield projects outward in a concave geometry from said handle body such that said outer periphery drapes toward said first end;

a junction of said shield with said handle body, said shield junction having a circular shoulder of transition that extends radially from said handle body, said shoulder is integrally connected to said shield;

at least two loops located diametrically opposed to one another on said outer periphery of said shield;

at least two connector projections diametrically opposed to one another on said external surface of said handle body, said connector projections project toward said first end, said connector projections located on said handle body in position to releasably receive thereon said loops on said periphery when said shield in bent toward said first end of said handle body;

a second end of said handle body, said second end opposite said first end, said second end having a generally cylindrical geometry and an exterior surface;

a threaded portion on said exterior surface of said second end, said threaded portion is integral with said handle body at said shield junction;

at least two elongated grooves originating at said first end, said grooves oriented along said exterior surface of said handle body, said grooves are located diametrically opposed to one another, said grooves extending axially toward said second end along said exterior surface, said grooves open outwardly both from said exterior surface and from said first end; and at least two insert projections on said exterior surface, said insert projections are located diametrically opposed to one another and aligned with said at least two elongated grooves, said insert projections extend along the axis of said handle body, each of said insert projections having a proximal end that extends toward said first end, said proximal end is proportioned to fit into one of said elongated grooves.

14. The disposable light handle of claim 13, wherein said at least two loops further comprise loops of suitable shape to readily and releasably engage respectively each one of said connector projections on said external surface of said handle body when said shield is bent into overlying relationship to said handle body.

15. The disposable light handle of claim 14, wherein each of said loops further comprise first and second legs, each leg having one of its ends integrally formed with said outer periphery of said shield and projecting therefrom, each leg having an outboard end integrally joined by a cross-member to define an opening to engage each of said connector projections.

16. The disposable light handle of claim 13, wherein said handle body of a first light handle is interconnectable to a second light handle having a second handle body of like design for purposes of minimizing space in the packaging and storage of disposable light handles, when the shields of said first light handle and said second light handle are bent in respective positions toward each handle body allowing said loops to attach over said respective connector projections, one of said elongated grooves on said first end of said first handle body accepts one of said insert projections of said second handle body when said second end of said second handle body is aligned toward said first end of said first handle body, thereby providing for two spaced apart and interconnected light handles for compact packaging and storage.

17. The disposable light handle of claim 13, wherein said threaded portion of said second end is releasably attachable to the existing threaded attachment means on the light fixture, whereby said shield provides a guard against contact between the hand of the user and the light fixture during attachment to, and movement of the light fixture.

18. A method of packaging at least two disposable light handles utilized for removable attachment to a manually adjustable light fixture of the type employed in medical treatment and operating rooms, each of the disposable light handles including a handle body having an elongated cylindrical shape having an external surface, a first end, and an opposite second end, the handle body joined along the length of the handle body with a generally circular shield integrally connected to the handle body, the shield having an outer periphery that projects outwardly in a concave geometry from the handle body when unbent, the outer periphery having at least two loops located diametrically opposed to one another on the periphery of the shield, the shield sufficiently flexible to be resiliently bent, and a connector means positioned at approximately mid-length of the handle body and aligned with each of the at least two loops, said method comprising the steps of:

providing a plurality of handle bodies, including a first handle body and a second handle body;

bending the resilient shield in an overlying position toward the first end of each handle body;

connecting the at least two loops to the connector means on each handle body to releasably receive thereon the loops on the bent shield of said bending step;

aligning the first end of said first handle body toward the second end of said second handle body with each shield bent in an overlying position toward each respective handle body;

attaching said second handle body to said first handle body by an attaching means; and packaging said attached handle bodies of said attaching step for compact storing and shipping of said light handles.

19. The method of packaging of claim 18, wherein said connecting means of said connecting step further comprises:

providing at least two connector projections diametrically opposed to one another on the external surface of each handle body, said connector projections positioned to releasably receive thereon the loops on the bent shield of said bending step; and placing the loops onto each respective connector projection, thereby releasably connecting the shield in bent overlying relationship toward the first end of each handle body.

20. The method of packaging of claim 19, wherein said attaching means of said attaching step further comprises:

providing at least two elongated grooves originating at each first end, said grooves oriented along said outer surface of each handle body, said grooves are located diametrically opposed to one another, said grooves open outwardly both from said outer surface and from said first end of each handle body; and inserting one of at least two insert projections on said outer surface of each handle body into one of said grooves, said insert projections located diametrically opposed to one another and aligned with said at least two elongated grooves, said insert projections extend along the axis of each handle body, each of said insert projections is proportioned to fit into one of said elongated grooves when said handle bodies are attached together.

21. A package of a plurality of disposable light handles having light handles attachable together within the package, the light handles utilizable for a manually adjustable light fixture of the type employed in medical treatment and operating rooms, the package comprising:

at least two handle bodies, each having an elongated generally cylindrical geometry, an outer surface, a first end, and a second opposite end;

a generally circular shield integrally formed separately with each handle body, each of said shields projecting generally radially outward from each of said handle body portions, each of said shields being sufficiently flexible to be resiliently bent in position toward each respective handle body when placed within the package;

an outer periphery of each of said shields, said shield projects outward in a concave geometry from said handle body such that said outer periphery drapes toward said first end when said handle bodies are not attached together;

at least two loops located diametrically opposed to one another on said outer periphery of each of said shields;

at least two connector projections diametrically opposed to one another on said outer surface of each handle body, said connector projections project toward each respective first end, said connector projections located on each handle body in position to releasably receive thereon said respective loops on each outer periphery when each shield is in bent position toward each respective first end of each handle body;

at least two elongated grooves originating at each first end, said grooves oriented along said outer surface of each handle body, said grooves are located diametrically opposed to one another, said grooves extending axially toward said second end along said outer surface, said grooves open outwardly both from said outer surface and from said first end of each handle body;

at least two insert projections on said outer surface of each handle body, said insert projections are located diametrically opposed to one another and aligned with said at least two elongated grooves, said insert projections extend along the axis of each of said handle body, each of said insert projections having a proximal end that extends toward said first end, said proximal end is proportioned to fit into one of said elongated grooves when said at least two handle bodies are attached together; and an enclosure within the package proportioned to enclose said at least two handle bodies attached together with said shields in bent position.

22. The package of a plurality of disposable light handles of claim 21, wherein said at least two loops further comprise loops of suitable shape to readily and releasably engage respectively each one of said connector projections on said outer surface of said handle body when said shield is bent into overlying relationship to said handle body.

23. The package of a plurality of disposable light handles of claim 22, wherein each of said loops further comprise first and second legs, each leg having one of its ends integrally formed with said shield periphery and projecting therefrom, each leg having an outboard end integrally joined by a cross-member to define an opening to engage each aligned connector projection.

24. In a disposable light handle including an elongated body portion having an outer surface, a closed end and an opposite end adapted to be attached to a light fixture for manipulation of the light, and a generally circular shield extending radially from the body portion at a location adjacent the opposite end of the light handle, the improvement comprising:

an elongated groove defined in the outer surface of the body portion, said groove originating at said closed end of the body portion and extending along a portion of the length of the body portion to terminate short of the shield, said groove having a cross-section having a perimeter which is continuous except for a single opening defined in the perimeter, said opening comprising less than one-half of the perimeter of said cross-section perimeter; and an elongated tongue projecting from the outer surface of the body portion at a location substantially opposite the location of said groove in the outer surface, said tongue originating adjacent the closed end of the body portion and extending along at least a portion of the length of the body portion, said tongue having a cross-section having a closed perimeter which is complementary to the cross-section of said groove whereby said tongue is receivable within said groove to releasably interconnect a first light handle to a second light handle of like design.

25. The improvement of claim 24, wherein said cross-section of said groove includes a perimeter defined by a first wall having opposite side edges disposed within the body portion and opposite side walls also disposed within the body portion and extending outwardly from said respective ones of said opposite side edges of said first wall, said opposite side walls converging toward one another in a direction outwardly of the body portion, said opposite side walls terminating at the outer surface of the body portion to define an elongated opening into said groove, and wherein said tongue includes a cross-section which is complementary with the cross-section of said groove and includes a web portion extending along the length thereof which is receivable within said elongated opening defined at the outer surface of the body portion of a light handle by the converging opposite side walls of said groove.

26. The improvement of claim 25, wherein said perimeter of said cross-section of said groove decreases in a direction away from the closed end of the body portion.

27. A disposable light handle for a manually adjustable light fixture of the type employed in medical treatment and operating rooms, said light handle comprising:

an elongated handle body portion including a multi-sided outer surface having a first side, a second side substantially diametrically opposed to said first side, a third side disposed between said first side and said second side, and a fourth side substantially diametrically opposed to said third side, said handle body portion having a closed outboard end, and an opposite end;

a generally circular shield integrally formed with said handle body portion proximate said opposite end, and extending generally radially from said handle body portion, said shield having an outer periphery of substantially uniform thickness over its area, and being sufficiently resiliently flexible as permits diametrically opposed portions of said periphery to be bent into overlying relationship to said handle body portion;

an elongated groove defined in said outer surface of said handle body portion and opening outwardly of said handle body portion, said groove originating at, and opening outwardly of, said closed end of said handle body portion and extending along a portion of the length of said handle body portion, said groove having a bottom wall disposed inwardly of said outer surface of said handle body portion and including opposite side walls which extend from opposite sides of said bottom wall outwardly of said handle body portion and inwardly of said groove; and an elongated tongue projecting from said outer surface of said handle body portion and extending from said closed end of said handle body portion along a portion of the length of said handle body portion, said tongue having an outboard surface which includes opposite side edges and which extends along substantially the length of said tongue, and including opposite side walls which extend from said opposite side edges of said outboard surface to said handle body portion and join said outboard surface to said handle body portion, said side walls diverging from one another from their respective joinder locations with said handle body portion to their respective joinder locations with said opposite side edges of said outboard surface of said tongue, whereby a tongue of a first light handle is receivable within a groove of a second light handle of like design to thereby releasably interconnect the first and second light handles to one another.

28. The disposable light handle of claim 27, wherein said light handle is a tubular handle body portion, and said end opposite said closed outboard end is open.

29. The disposable light handle of claim 27, wherein said light handle further comprises:

first and second attachment means disposed on said periphery of said shield at substantially diametrically opposed locations, said first attachment means aligned with said first side, and said second attachment means aligned with said second side; and first and second connector projections disposed at respective substantially diametrically opposed locations on said first side and said second side respectively on said handle body portion and spaced along the length of said handle body portion a distance suitable for releasably engagement of said first and second attachment means on said shield with respective ones of said first and second connector projections disposed on said handle body portion.

30. The disposable light handle of claim 27, wherein the perimeter of said cross-section of said groove decreases in a direction away from said closed end of said handle body portion.

31. The disposable light handle of claim 30, wherein said groove terminates as a ledge.

32. The disposable light handle of claim 31, wherein said ledge is located in spaced apart relationship to said shield.

33. The disposable light handle of claim 27, wherein said groove of one light handle and said tongue of a further light handle of like design define complementary elements of a conventional tongue and groove interconnection.

34. The disposable light handle of claim 27, wherein said handle is tubular and said groove includes an open end at said closed end of said tubular handle body portion, said open end of said groove opening outwardly of said closed end of said tubular handle body portion, and wherein said tongue includes an end which is disposed substantially flush with said closed end of said tubular handle body portion.

35. The disposable light handle of claim 34, wherein said groove is of a decreasing cross-sectional area in a direction from said closed end of said tubular handle body portion toward said terminal ledge of said groove.

* * * * *